(12) United States Patent
Schmera et al.

(10) Patent No.: US 9,645,101 B2
(45) Date of Patent: May 9, 2017

(54) BACTERIA IDENTIFICATION BY PHAGE INDUCED IMPEDANCE FLUCTUATION ANALYSIS

(71) Applicants: Gabor Schmera, San Diego, CA (US); Laszlo Kish, College Station, TX (US)

(72) Inventors: Gabor Schmera, San Diego, CA (US); Laszlo Kish, College Station, TX (US)

(73) Assignee: The United States of America, as Represented by the Secretary of the Navy, Washington, DC (US)

(*) Notice: Subject to any disclaimer, the term of this patent is extended or adjusted under 35 U.S.C. 154(b) by 382 days.

(21) Appl. No.: 13/936,631

(22) Filed: Jul. 8, 2013

(65) Prior Publication Data
US 2013/0295556 A1 Nov. 7, 2013

Related U.S. Application Data

(63) Continuation-in-part of application No. 13/075,250, filed on Mar. 30, 2011, now abandoned.

(51) Int. Cl.
| | | |
|---|---|---|
| *G01N 27/02* | (2006.01) | |
| *G01N 33/569* | (2006.01) | |
| *G01N 33/487* | (2006.01) | |

(52) U.S. Cl.
CPC ..... *G01N 27/021* (2013.01); *G01N 33/48735* (2013.01); *G01N 33/56911* (2013.01)

(58) Field of Classification Search
CPC ........... G01N 27/021; G01N 33/48735; G01N 33/56911
See application file for complete search history.

(56) References Cited

U.S. PATENT DOCUMENTS

| 7,229,754 B2 | 6/2007 | Kish et al. | |
|---|---|---|---|
| 2005/0208592 A1* | 9/2005 | Caron et al. | 435/7.1 |

(Continued)

OTHER PUBLICATIONS

Dobozi-King et al., Rapid Detection and Identification of Bacteria: Sensing of Phage-Triggered Ion Cascade (SEPTIC), Journal of biological Physics and Chemistry, 2005, 5:3-7.

(Continued)

*Primary Examiner* — Melanie Y Brown
(74) *Attorney, Agent, or Firm* — SSC Pacific Patent Office; Arthur K. Samora; Kyle Eppele

(57) ABSTRACT

Methods for detection and identification of bacteria within a sample include the step of inserting a pair of electrodes into the sample. A first impedance across the electrodes is established with a first AC voltage source having a first frequency. A phage is introduced into the sample, and impedance fluctuations that are caused by ion release by the bacteria due to the phage introduction are measured. The use of impedance fluctuations instead of voltage fluctuations to detect and identify bacteria minimizes 1/f noise effects and increases system sensitivity. To further increase system sensitivity by eliminating thermal noise, a second impedance across the electrodes can be established using a second AC voltage source at a second frequency. Second impedance fluctuations are cross-correlated to the first impedance fluctuations, and the cross-correlation results are analyzed to determine whether or not bacteria are present in the sample based on phage electrical activity.

2 Claims, 4 Drawing Sheets

(56) References Cited

U.S. PATENT DOCUMENTS

2009/0068638 A1     3/2009    Shabani et al.
2009/0202985 A1*   8/2009    Gulak ..................... C12Q 1/18
                                                                                  435/5

OTHER PUBLICATIONS

Kish et al., Bacteria Identification by Phage Induced Impedance Fluctuation Analysis (BIPIF), Sensors & Transducers, vol. 149, Issue 2 (Feb. 2013), pp. 174-178.

* cited by examiner

BACTERIA IDENTIFICATION BY PHAGE INDUCED IMPEDANCE FLUCTUATION ANALYSIS

CROSS-REFERENCE TO RELATED APPLICATIONS

This application is a continuation-in-part of U.S. application Ser. No. 13/075,250, filed Mar. 30, 2011 (NC 100811), and entitled "Bacteria Identification by Phage Induced Impedance Fluctuation Analysis". The '250 application is hereby incorporated by reference herein in their entirety.

FEDERALLY-SPONSORED RESEARCH AND DEVELOPMENT

This invention (Navy Case No. 102601) is assigned to the United States Government and to The Texas A&M University System, and it is available for licensing for commercial purposes. Government licensing and technical inquiries may be directed to the Office of Research and Technical Applications, Space and Naval Warfare Systems Center, Pacific, Code 72120, San Diego, Calif. 92152; voice (619) 553-5118; e-mail ssc pac t2@navy.mil. The Texas A&M University System licensing and technical inquiries may be directed to Texas A&M System Technology Commercialization, 800 Raymond Stotzer Parkway, Suite 2020 TIPS Bldg, m/s 3369 TAMU, College Station, Tex. 77845-6151; e-mail cschwartze@tamus.edu.

FIELD OF THE INVENTION

The present invention applies generally to bacteria detection systems. More specifically, some embodiments of the invention pertain to systems and methods for the detection of bacteria within a sample by introducing a phage into the sample and then measuring the resulting phage-induced impedance fluctuations across the sample.

BACKGROUND OF THE INVENTION

Fluctuation-Enhanced chemical and biological Sensing (FES) is known in the prior art. FES can be based on stochastic analysis and simulation and utilizes the stochastic component of sensor signals that can be caused by the statistical interaction between the sample being tested and the sensor. A typical FES system utilizes specially designed sensors, advanced signal processing and pattern recognition algorithms to measure electrical fluctuations in the sample, which can be caused by ion release due to disintegration and/or dissolution of bacteria during an induced phage infestation.

Many prior art FES methods for detecting and identifying bacteria are based on the detection and analysis of direct current (DC) voltage fluctuations, which are caused by the stochastic emission of ions during phage infection of a sample. For these systems and methods, a two-electrode nano-well device can be immersed in the carrier fluid containing a phage-infected sample and the microscopic voltage fluctuations are measured across the electrodes.

However, prior art methods that measure DC voltage fluctuations can have some fairly significant disadvantages. More specifically, these methods have not been shown to work for small bacterium numbers; all experiments so far used large samples (typically on the order of 10 million bacteria per sample). This can be because these techniques measure fluctuations in the DC electrical field; i.e., the underlying and assumed phenomenon can be the separation of positive and negative ions. Second, prior art DC FES system sensitivities can be limited by the presence of strong 1/f background noise (pink noise). Additionally, drift, aging of the electrode material and dependence on surface effects and corrosion can further degrade the performance of these types of systems.

In view of the above, it can be an object of the present invention to provide systems and methods for detecting and identifying bacteria in a sample by measuring impedance fluctuations due to phage infestation of the sample. Still another object of the present invention is to provide a bacteria identification by phage induced impedance fluctuation (BIPIF) analysis method with a much faster response time than the measuring methods of the prior art. Yet another object of the present invention is to provide BIPIF methods that can measure bacteria in a sample before the lysis of the bacteria by the phage that has been introduced into the sample. Still another object of the present invention is to provide a BIPIF methods with a sensitivity that is below the pink noise thresholds of direct current (DC) systems in the prior art. Another object of the present invention can be to provide systems and methods for detecting and identifying bacteria in a sample that offers several orders of magnitude improvement in sensitivity and higher reproducibility, at the expense of somewhat more sophisticated sensor circuitry and signal processing algorithms. Yet another object of the present invention can be to provide systems and methods for detecting and identifying bacteria in a sample that use alternating current (AC) impedance, so that the systems and methods work even when the negative and positive ions in the sample are in balance. Still another object of the present invention can be to provide systems and methods for detecting and identifying bacteria in a sample that increases detection sensitivity by minimizing the effect of noise sources such as 1/f noise, thermal noise and amplifier noise.

SUMMARY OF THE INVENTION

Methods and systems for accomplishing the methods for the detection and identification of bacteria within a sample according to several embodiments of the present invention can include the initial step of inserting a pair of electrodes into the sample so that the electrodes are in contact with the sample (Alternatively, the sample could be place in contact with structure containing the electrodes. Additionally, sensor other than electrodes could be used, provided the sensors can detect and measure impedances). The methods and systems can further include the step of establishing a first impedance across the electrodes with a first alternating current (AC) voltage source, with the first AC source having a first frequency ($f_1$).

The methods and systems can further include introducing a phage into the sample. As the phage causes the disintegration and/or dissolution of bacteria (if any) in the sample, the methods and systems can measure the impedance fluctuations of the sample which are caused by ion release by the bacteria during the phage infestation. The measurement of the impedance fluctuations can be used to determine if bacteria can be present in the sample. One way to do this could be to compare the impedance fluctuation pattern to a reference impedance fluctuation pattern of the sample, which was taken when the sample was known to be bacteria free.

To measure the resulting impedance fluctuations, the systems and methods can include the use of a lock-in amplifier that can be connected to the electrodes. A pattern generator can be connected to the lock-in amplifier, and a pattern recognizer can be connected to the pattern generator. The pattern generator and recognizer can include processors that have a non-transitory medium that contains instructions for carrying out the methods of the present invention, according to several embodiments. The pattern recognizer can have access to a database of previously recorded impedance fluctuation patters that were measured and generated from known samples.

The use of an AC source at a relatively high frequency ($f_1 \approx 10$ kHz) and measurement of impedance fluctuations across the sample can allow for much greater sensitivity for the methods by avoiding the 1/f noise at the electrode surfaces. To further increase the sensitivity by avoiding thermal noise, the methods (and systems for accomplishing the methods) can include the step of establishing a second impedance across said electrodes with a second AC voltage source having a second frequency ($f_2$). This can establish a second impedance fluctuation across the electrodes. In several embodiments, the second impedance fluctuations can be measured and cross-correlated to the first impedance fluctuations resulting from application of the first AC voltage. The cross-correlation results can used to generate impedance fluctuation patterns that can be further analyzed to determine whether or not bacteria can be present in the sample based on phage electrical activity. Some representative phages that can be used in the systems and methods presented herein can include the T5 and Ur-λ phages.

BRIEF DESCRIPTION OF THE DRAWINGS

The novel features of the present invention will be best understood from the accompanying drawings, taken in conjunction with the accompanying description, in which similarly-referenced characters refer to similarly referenced parts, and in which.

DETAILED DESCRIPTION OF THE EMBODIMENTS

Figure 1:
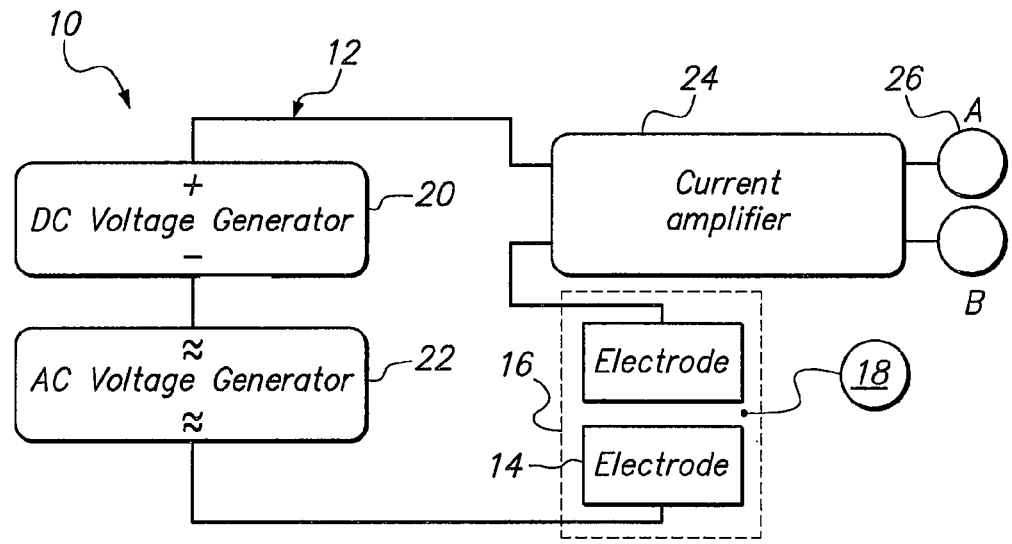
FIG. 1 can be an exemplary system for detecting and identifying bacteria in a sample using phage induced impedance analysis, according to several embodiments of the present invention.

Referring now to the Figures, FIG. 1 illustrates the system 10 for identifying bacteria in a sample using phage induced impedance fluctuation analysis, according to several embodiments of the present invention. As shown in FIG. 1, the system 10 can include an electrical circuit 12. Circuit 12 can include a pair of electrodes 14 that are inserted into the sample 16 to be tested. A phage 18 can be introduced into the sample 16. As the phage interacts with the bacteria, the disintegration/dissolution of the bacteria (if any) in the sample creates electrical activity. That electrical activity can be measured and interpreted to determine whether (or not) there can be bacteria in the sample 16. The manner in which this can be accomplished, as well as the structure of circuit 12, can be described more completely below.

As shown in FIG. 1, circuit 12 can include a direct current (DC) voltage generator 20. The role of the DC voltage generator 20 can be to apply a DC voltage across electrodes 14 to attract the bacteria to one of the electrodes 14. The system 10 of the present invention can further include an alternating current (AC) voltage generator 22. AC generator 22 can be used to apply an AC voltage across circuit 12, which can allow for AC impedance fluctuation measurements across electrodes 14. With this configuration, the interference from 1/f noise in the electrical Coulomb field at the surfaces of electrodes 14 can be avoided by using an AC voltage source having a relatively high probing frequency (such as 10 KHz). The 1/f noise, which can be caused by the DC potential fluctuations in the vicinity of the electrodes, can be the primary sensitivity limiting factor for DC systems and methods that are known in the prior art.

Figure 2:
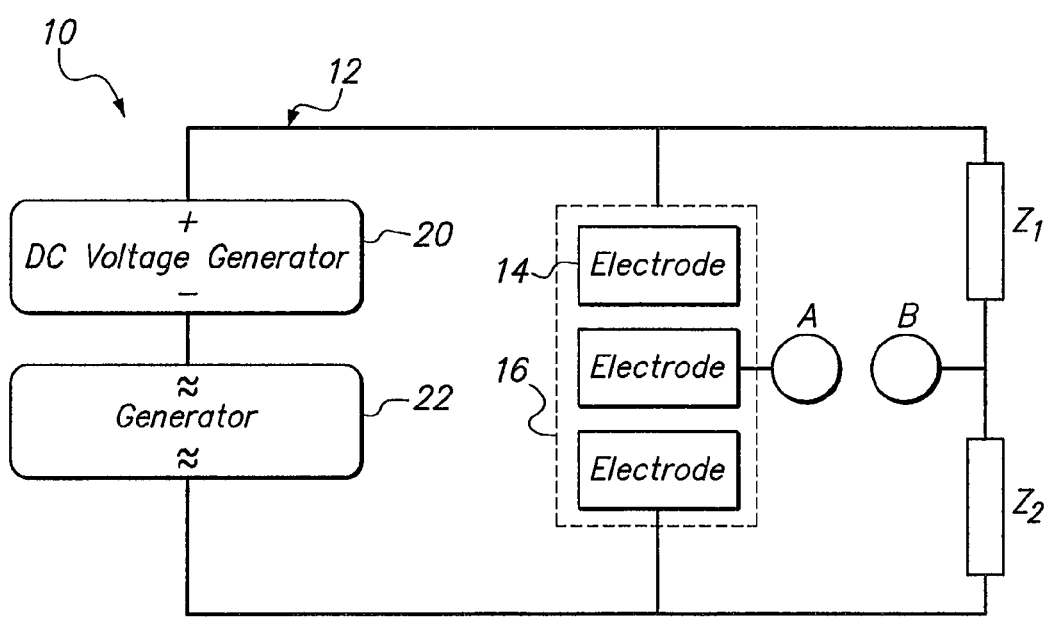
FIG. 2 can be the same system as FIG. 3, but with the sample electrodes in a bridge arrangement according to several embodiments.

FIG. 1 illustrates a relatively simple realization of the systems according to several embodiments of the present invention, with two electrodes 14 inserted into sample 16. With this configuration, fluctuations in impedance across electrodes are measured. In several alternative embodiments, however, and as shown in FIG. 2, the electrodes 14 can be arranged within circuit 12 and inserted into sample 16 in a bridge arrangement. In some embodiments, similar arrangements with more than three electrodes are possible.

Figure 3:
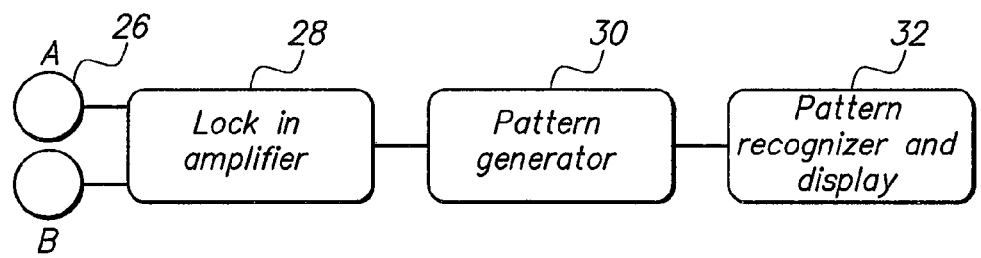
FIG. 3 can be a continuation of the system illustrated in FIGS. 1 and 2 from connection points A and B.

The impedance fluctuations across the electrodes 14 can be measured using additional components that are connected to connection points 26 in FIGS. 1 and 2. To facilitate the measurement of the impedance fluctuation, a current amplifier 24 can be included in circuit 12. Next, and as shown in FIG. 3, connection points 26 can be connected to the differential input of a lock-in amplifier 28. Stated differently, amplifier 24 can interconnect electrodes 14 and lock-in amplifier 28 in circuit 12. Lock-in amplifier 28 can further be connected to a pattern generator 30 (such as a spectrum analyzer, for example), and a pattern recognizer 32 can be connected to pattern generator 30. Pattern generator 30 and pattern recognizer 32 can include processors that have non-transitory computer readable medium. The computer readable medium can contain computer instructions for accomplishing the methods according to several embodiments of the present invention. Pattern recognizer 32 can further have access to a database and/or data store (not shown in the Figures) of previously recorded impedance fluctuation patterns that were measured and generated from known samples. The lock-in amplifier 28, pattern generator 30 and pattern recognizer 32 can be driven by the same AC voltage generator 22 that can be connected to the electrodes 14.

As stated above, utilizing the AC voltage generator 22 and measuring the conductance fluctuations across the electrodes 14 can result in a significantly higher sensitivity compared to the prior-art methods where DC field fluctuations are measured. By properly setting the time-constant of the lock-in amplifier 28, its output will provide a slowly fluctuating AC signal that is proportional to the low-frequency conductance fluctuations of the sample 16, which are due to electrical activity caused by the introduction of phage 18 into sample 16.

In order to further improve the performance of the system, it can be desirable to reduce the interference caused by thermal noise and by the amplifier noise. This can be accomplished by establishing a second AC voltage across the circuit 12. To do this, a second AC source 22 (not shown) can be connected to circuit 12 at a different frequency $f_2$ than frequency $f_1$. Additionally, and referring now to FIG. 4, an additional lock-in amplifier 28b can be attached to connection points 26 and synchronized to frequency $f_2$. Cross-correlating pattern generator 34 (for example, a cross-spectrum analyzer) can be connected to lock-in amplifiers 28 and the aforementioned pattern recognizer 32 can be connected to cross-correlating pattern generator 34. By using two separate frequencies, a sufficiently large AC drive current and cross correlation measurements, the thermal noise and amplifier noise can also be reduced. By fine-tuning these system parameters, detecting and identifying a single infected bacterium becomes a possibility.

In order to quantitatively estimate the improvement in sensitivity by the systems and methods according to several embodiments, an analysis and comparison of the signal strengths produced by the methods according to several embodiments and the DC methods described in the prior art can be disclosed. It can be seen how the presence of 1/f noise (and thermal noise) limits the sensitivity of both systems.

The DC methods of the prior art can be based on a concentration cell (two electrodes of identical metals with fluctuating electrolyte concentration). The voltage $U_{cc}$ generated by a concentration cell can be described by the Nernst equation:

$$U_{cc} = \frac{kT}{Zq} \ln \frac{n_2}{n_1} \quad (1)$$

where k can be the Boltzmann constant, T can be the absolute temperature, Z can be the valence number of the ions, q can be the charge of an electron, and $n_1$ and $n_2$ are the ion concentrations in the vicinity of the electrodes. At room temperature, Eq. 1 reduces to:

$$U_{cc} = \frac{0.26}{Z} \ln \frac{n_2}{n_1} \; [\text{Volt}] \quad (2)$$

Now let $n_n = n_1 + \Delta n$ represent the change in concentration at an electrode 14 that can be caused by an infestation of phage 16. Assuming small relative concentration change, $|\Delta n| \ll n_1$, the observed voltage fluctuation during DC measurements in the prior art can be:

$$\Delta U_{sep} = \frac{kT}{Zq} \ln\left(\frac{n_1 + \Delta n}{n_1}\right) = \frac{kT}{Zq} \ln\left(1 + \frac{\Delta n}{n_1}\right) \approx \frac{kT}{Zq} \frac{\Delta n}{n_1} = \frac{0.026}{Z} \frac{\Delta n}{n_1} \quad (3)$$

To estimate the voltage fluctuations when using the AC methods according to several embodiments, the ion concentrations at one of electrodes 14 are used. Here too, the ion concentrations in the vicinity of the electrodes will determine the conductance and its fluctuations even under anisotropic conditions. For sake of simplicity, it can be assumed that a single AC current generator can be used; then the observed voltage fluctuations that are due to conductance fluctuations during measurement according to the systems and method of the present invention according to several embodiments can be simply:

$$\Delta U_{bip} = U_0 \frac{\Delta n}{n_1} \quad (4)$$

(This analysis assumes that the electrodes 14 are approximately the same size). It can be evident from equations (3) and (4) that characteristics of the signals measured by the two methods are very similar. However, the methods of the present invention according to several embodiments produce significantly higher signal levels (and drastically reduced noise levels) for the reasons as stated below.

To measure the improvement or gain (G) in signal strength (power) by the squared ratio of the measured voltage fluctuations for the systems and methods of the present invention, over the prior art DC methods, let $\Delta U_{bip}$ represent voltage fluctuations for the systems of the present invention and let $\Delta U_{sep}$ represent voltage fluctuations for the DC systems and methods of the prior art:

$$G = \left(\frac{\Delta U_{bip}}{\Delta U_{sep}}\right)^2 = \left(\frac{U_0 Z}{0.026}\right)^2 \quad (5)$$

As a concrete example, consider magnesium ions (Z=2) and 1 V effective AC voltage ($U_0$=1.41V) drop between electrodes 14 (this value can be proven to give Ohmic response with electrolytes); then the gain obtained is:

$$G = \left(\frac{\Delta U_{bip}}{\Delta U_{sep}}\right)^2 = \left(\frac{1.41 * 2}{0.026}\right)^2 > 11700 \quad (6)$$

Thus, the signal power using the AC methods of the present invention according to several embodiment can increase the system 10 sensitivity by four orders of magnitude over the DC systems of the prior art.

Figure 5:
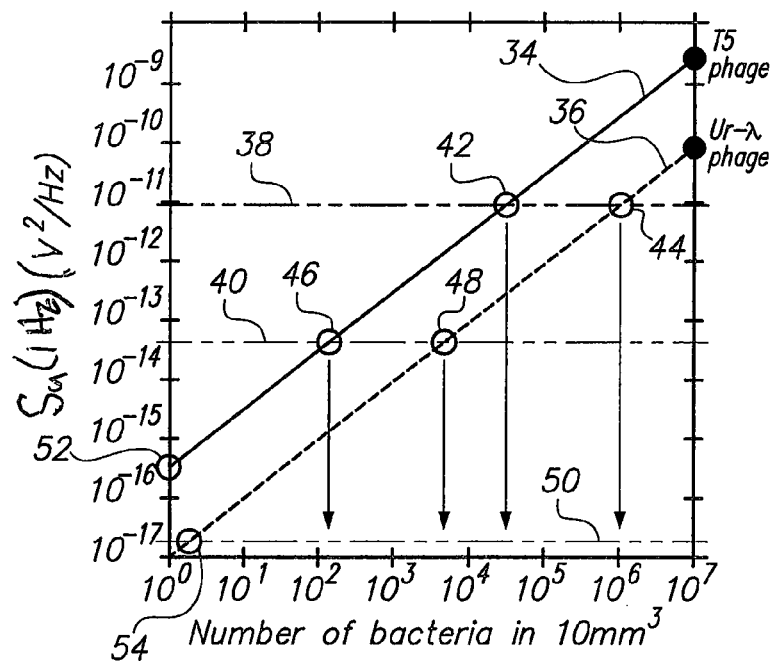
FIG. 5 can be a graph that depicts the performance of the system and methods of the present invention according to several embodiments, when compared to prior art direct current (DC) systems.

FIG. 5 is a graph of the power spectrum of the measured voltage fluctuations at 1 Hz (Su (1 Hz) in V²/Hz) for a sample of 10 mm² with *E. coli* bacteria present, which is plotted as a function of the number of *E. coli* bacteria present in the sample volume. FIG. 5 can be used to illustrate the increased sensitivity of the bacteria identification by phage induced impedance fluctuation (BIPIF) methods of the present invention due to the virtual elimination of 1/f voltage noise interference (The 1/f noise that is caused by charge density fluctuations at the electrodes when a DC voltage is applied across the electrodes.). It should be appreciated that FIG. 5 represents measured values with respect to prior art measuring systems. However, it can also be used to demonstrate and explain the sensitivity limits of BIPIF. FIG. 5 assumes linear sensor response with respect to the power density spectrum versus the number of bacteria. This assumption is justified as long as the individual bacteria act as independent sources of fluctuations.

The prior art methods can measure the fluctuations in the DC electric field. In this case, the voltage fluctuations in the nanowell 16 can be measured and the power spectrum value of these fluctuations at 1 Hz is plotted. Line 34 represents the sensor response using the T5 phage for prior art systems. Line 36 can represent the sensor response using the Ur-A phage. In both cases, the sensitivity (horizontal line 38) can be limited by the 1/f voltage noise (pink noise).

The BIPIF methods according to several embodiments can measure the output of the lock-in amplifier 28 (voltage) from FIG. 3. The voltage response from amplifier 28 can be proportional to the impedance fluctuations of the nanowell 16 in a bridge arrangement. Using the voltage response, the power spectrum can be generated in a manner known in the art. In this case the voltage 1/f noise will not play a measurable role for two reasons: 1) The driving AC frequency is high enough (10 kHz for instance) so that the 1/f noise strength is negligible at this frequency; and, 2) The 1/f noise is not correlated with the driving AC frequency.

It can be assumed that the power spectrum of the signal at 1 Hz is the same as in the prior art (the power spectrum response of the infected sample is the same; it is simply being measured differently). If the response of the sample to the introduced phage is the same, then the measurement methods of the present invention would not be limited by the pink noise line 38 in FIG. 5. Instead, the measurement method of several embodiments would be limited by the thermal noise of the system, which is indicated by line 40 in FIG. 5. For the T5 phage, this would mean an improvement in sensitivity from about $3\times10^4$ bacteria in the prior art (point 42 in FIG. 5) to ~140 bacteria (point 46 in FIG. 5). With this configuration, the methods of the present invention are able to measure impedance fluctuations (by measuring voltage fluctuations at amplifier 28 and converting to impedance fluctuations) that are below the pink noise threshold. The limiting factor then becomes the thermal noise (again represented by line 40 in FIG. 5), which implies a larger than three orders of magnitude improvement in sensitivity for the methods of the present invention.

Note that the detection limits for the systems and methods according to several embodiments can be further lowered when a second AC voltage source, second lock-in amplifier 28b and cross-correlating pattern generator 34 of the present invention according to several embodiments described above are used to mitigate the effects of white noise sources such as thermal noise and amplifier noise, and the sensitivity can be lowered. Combining this result with the signal strength gain (Eq. 6) we see that BIPIF will improve sensitivity by up to 7 orders of magnitude. Thus, the systems and methods according to several embodiments can improve sensitivity by three to four orders of magnitude due to the elimination of 1/f noise, as well as the elimination of thermal noise, as a limiting factor. The sensitivity limited then becomes lowered to line 50 in FIG. 5.

Equations (1)-(6) and FIG. 5 above illustrate that the present invention measurement methods can be based on fast stochastic impedance fluctuations that occur when the phage in introduced into the sample. One of the advantages of the BIPIF of the present invention according to several embodiments, when compared to the prior art, is that in the prior art, a shift in the impedance value (a slow impedance-drift) is used to detect the presence of bacteria. The present invention methods take advantage of a stochastic phenomenon, the fast conductance fluctuations. The BIPIF does not detect or use a slow deterministic impedance-shift. Instead, the methods of the present invention according to several embodiments take advantage of the rapid stochastic (i.e., non-deterministic) movement around a mean impedance value of the sample.

The BIPIF of the present invention provides the additional advantage of measuring fast stochastic micro-fluctuations around the (deterministic) impedance value, which are caused by the ion cascade (scream) during the first few minutes of the infestation of living bacteria, i.e. before lysis. Thus, the BIPIF methods can detect the bacteria before lysis of the bacteria by the phage. This is different from the prior art methods, which measure the slow deterministic shift in overall impedance that during lysis. The impedance shift can be caused by the massive amount of dead bacteria $-\frac{1}{2}$ to 1 hour after infestation. Stated differently, the methods of the present invention can be used to detect bacteria up within 1-2 minutes after introduction of the phage into the sample, as opposed to the up to one hour wait time that is required by the methods of the prior art.

Figure 6:
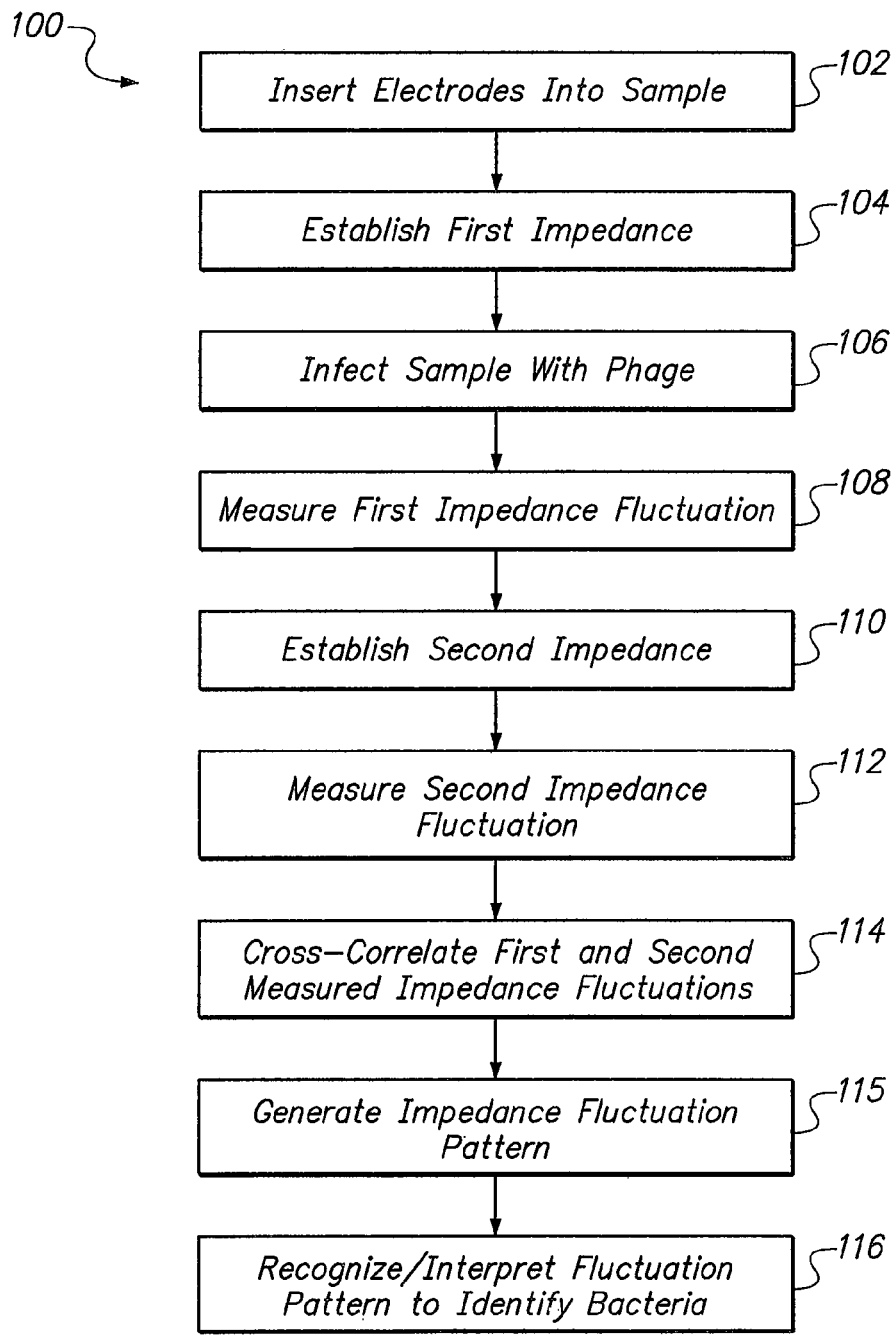
FIG. 6 can be a flowchart outlining an exemplary process for accomplishing the methods of detecting and identifying bacteria in a sample, according to several embodiments of the present invention.

FIG. 6 can be a flowchart that can be illustrative of the methods according to several embodiments of the present invention. Method 100 in FIG. 6 can include the initial step 102 of inserting at placing two electrodes 14 in contact with sample 16. One way to accomplish this step could be to insert electrodes 14 into sample 16. The step could also be accomplished with a component other than electrodes 14, provided the component can measure impedances. This step 102 can also be accomplished with the aforementioned bridge arrangement of electrodes 14. Once the electrodes are contacting the sample, the methods can include the step of establishing a first impedance across electrodes 14, as indicated by step 104 in FIG. 6. This can be accomplished through the use of a first AC voltage source 22 at frequency $f_1$. Once an impedance is established, the methods can further include the step 106 of infecting sample 16 by introduction of phage 18.

As the phage 18 causes the disintegration/dissolution of the bacteria in the sample, electrical activity can be generated in the sample. The measurement of that electrical activity can be accomplished by measuring fluctuations in the first impedance, as indicated by step 108 in FIG. 6. The measured impedance fluctuations can be synchronized using a lock-in amplifier, and the resulting impedance fluctuation pattern can be input into a pattern generator 30 and pattern recognizer 32 as described above.

Figure 4:
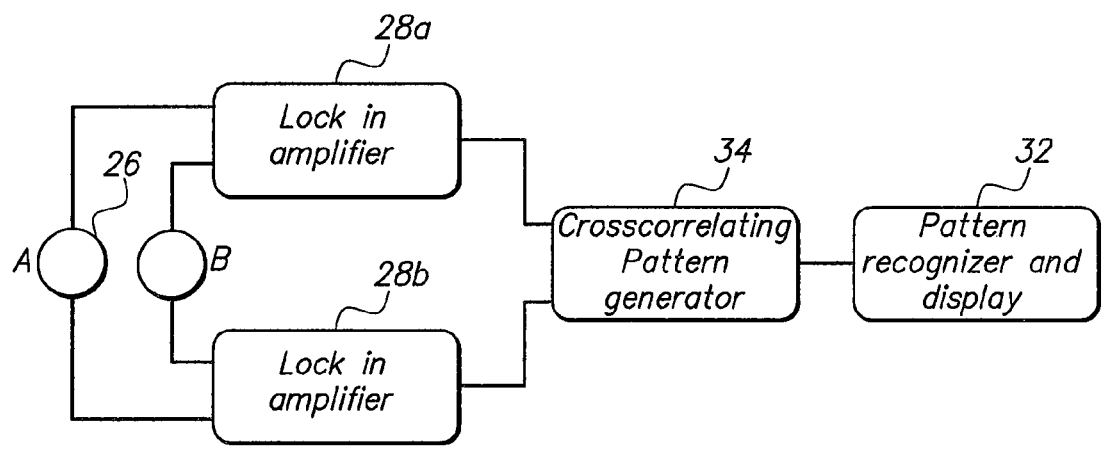
FIG. 4 can be an alternative embodiment of the portion of the system shown in FIG. 3, which further illustrates how two alternating current (AC) voltage sources at frequencies $f_1$ and $f_2$ can be used to practice the methods according to several embodiments.

To further mitigate the effects of thermal noise, a second AC voltage source at $f_2$ can optionally be added as described above. This establishes a second impedance across electrodes 14, as illustrated by optional step 110 in FIG. 6. After the phage 18 is introduced into sample 16, a step 110 is accomplished if desired, a second impedance across electrodes 14 can be measured, as indicated by block 112. The second impedance can be synchronized at frequency $f_2$ using a second lock-in amplifier, as shown in FIG. 4. For these embodiments, the first and second impedances can be cross-correlated, as shown by step 114 in FIG. 6. This can be accomplished using the cross-correlating pattern generator 34 in FIG. 4. The correlated fluctuation pattern result can be sent to a pattern recognizer as described above, and for further display to the user.

Once an impedance fluctuation has been measured, an impedance fluctuation pattern can be generated by a pattern generator 30, as described above and as shown by step 115 in FIG. 6. This can occur both in embodiments where only one impedance is generated and also in the embodiment where two or more impedances are generated. For embodiments where two impedances are generated at different frequencies, a cross-correlating pattern generator 34 can be used.

Once an impedance fluctuation pattern has been generated as described above, the methods according to several embodiments can include the step of recognizing the generated impedance fluctuation patterns, as described above and depicted by step 116 in FIG. 6. This step can be accomplished by comparing the measured impedance fluctuation pattern with stored patterns in a database that correspond to impedance fluctuation patterns of known phage-infected bacteria.

The aforementioned enhanced procedure can be used to detect the presence of bacteria. As disclosed above, this embodiment can further enhance sensitivity by reducing interference from thermal noise and from detector noise. The procedure can include the steps of: Inserting the electrodes into the sample. Once the electrodes are inserted, the user can measure first impedance fluctuations at the frequency of first AC generator ($f_1$) using the first lock-in amplifier (the first lock-in amplifier is synchronized to the first AC generator). Next, the user can measure second impedance fluctuations at the frequency of second AC ($f_2$) generator using the second lock-in amplifier (The second lock-in amplifier is synchronized to the second AC generator).

Once the first and second impedance fluctuations are measured, the user can use a cross-correlational pattern generator (such as a cross-spectrum analyzer) to generate a first cross-correlational pattern. Next, the phage can be introduced to the sample. After introduction of the phage, third impedance fluctuations at the frequency of first AC generator ($f_1$) using the first lock-in amplifier can be measured. Fourth impedance fluctuations at the frequency of the second AC generator ($f_2$) can be measured using the second lock-in amplifier, which can be synchronized to the second AC generator.

Once the third and fourth impedance fluctuations are measured, a cross-correlational pattern generator (such as a cross-spectrum analyzer) can be used to generate a second cross-correlational pattern, and the first and second cross-correlational patterns can be compared to determine the presence of bacteria. All steps can be automated by using standard programming tools such as Matlab, for example.

For identification of the bacteria, the measurement process could be similar. A library of power density spectrum patterns could be created by using sample containing known bacteria types. Then the power density spectrum of the unknown bacteria could be compared with the stored power spectrum densities and if a close match is found (within predetermined parameters set by the user), the identification could be made; if a close match is not found, the sample could be labeled as "unknown type". In embodiments where two AC generators are used, cross-correlational patterns could be used in place of power spectrum densities to identify the bacteria.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value can be incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, can be intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof can be encompassed by the invention unless otherwise indicated herein or otherwise clearly contradicted by context.

What is claimed is:

1. A method of detecting bacteria within a sample, comprising:
    inserting a pair of electrodes into said sample;
    establishing a direct current voltage across said pair of electrodes;
    superimposing a first alternating current voltage source across said electrodes, superimposing comprising providing the first alternating current voltage source as having a first frequency in a range of at least approximately 1000 Hz, said first alternating current voltage source establishing a first impedance across said pair of electrodes;
    infecting said sample with a phage selectably reactable with said bacteria, infecting comprising establishing fluctuations in said first impedance by way of reacting said phage with said bacteria, thereby providing said first impedance fluctuations;
    generating, by a pattern generator having a pattern generator processor operating under a set of instructions storable in relation to a pattern generator nontransitory medium, a first impedance pattern based on said first impedance fluctuations prior to lysis of said bacteria; and
    comparing, by a pattern recognizer having a pattern recognizer processor operating under a set of instructions storable in relation to a pattern recognizer nontransitory medium, said first impedance pattern with previously-recorded impedance fluctuation patterns storable in a database from known samples, thereby indicating presence of said bacteria in said sample when said first impedance pattern matches one of the previously-recorded impedance fluctuation patterns.

2. The method of claim 1, wherein superimposing comprises providing the first alternating current voltage source as having said first frequency comprising approximately 10 kHz.

* * * * *